United States Patent [19]

Lawson

[11] Patent Number: 5,243,047
[45] Date of Patent: Sep. 7, 1993

[54] TRIAZOLE/THIAZOLE AMINO-S-TRIAZINE BONDING AGENTS

[75] Inventor: John R. Lawson, Manchester, England

[73] Assignee: Imperial Chemical Industries PLC, London, England

[21] Appl. No.: 614,896

[22] Filed: Nov. 16, 1990

Related U.S. Application Data

[62] Division of Ser. No. 301,785, Jan. 25, 1989, Pat. No. 4,978,756.

[30] Foreign Application Priority Data

Feb. 15, 1988 [GB] United Kingdom ............... 8803477
Aug. 5, 1988 [GB] United Kingdom ............... 8818708

[51] Int. Cl.$^5$ ............... C07D 253/02; C07D 249/04; C07D 249/16; C07D 249/18
[52] U.S. Cl. ............................ 544/198; 548/255; 548/257; 548/260; 548/152; 548/161; 548/163
[58] Field of Search ............... 549/198; 548/255, 257, 548/260, 152, 161, 163

[56] References Cited

U.S. PATENT DOCUMENTS

| | | | |
|---|---|---|---|
| 3,277,065 | 10/1966 | Petropoulos et al. | 526/227 |
| 3,562,158 | 2/1971 | Varsanyi | 544/158 |
| 3,642,813 | 2/1972 | Kirchmayr et al. | 548/255 |
| 3,837,964 | 9/1974 | Cotton et al. | 156/182 |
| 3,894,019 | 7/1975 | Westlinning et al. | 544/197 |
| 3,928,344 | 12/1975 | Westlinning et al. | 544/197 |
| 4,026,890 | 5/1977 | Wulfers | 544/197 |
| 4,112,238 | 9/1978 | Chapman et al. | 560/70 |
| 4,169,112 | 9/1979 | Elmer et al. | 523/200 |
| 4,283,460 | 8/1981 | Shemenski | 428/389 |
| 4,284,536 | 8/1981 | Bezwada | 524/106 |
| 4,299,640 | 11/1981 | Erickson | 428/292 |
| 4,300,973 | 11/1981 | Bezwada | 156/307.7 |
| 4,428,987 | 1/1984 | Bell et al. | 427/327 |
| 4,448,847 | 5/1984 | Bell et al. | 428/413 |
| 4,514,398 | 4/1985 | Regnier et al. | 544/198 |

FOREIGN PATENT DOCUMENTS

| | | |
|---|---|---|
| 0126030 | 5/1984 | European Pat. Off. |
| 0134699 | 8/1984 | European Pat. Off. |
| 0137987 | 8/1984 | European Pat. Off. |
| 1419632 | 4/1972 | United Kingdom . |
| 1504375 | 6/1975 | United Kingdom . |
| 1419631 | 12/1975 | United Kingdom . |
| 2032807 | 10/1979 | United Kingdom . |
| 2037617 | 11/1979 | United Kingdom . |
| 1575516 | 9/1980 | United Kingdom . |
| 2104107 | 8/1982 | United Kingdom . |

OTHER PUBLICATIONS

Chemical Abstracts 99, 21687e 1982.
Chemical Abstracts 98, 187966h 1982.
Chemical Abstracts 91, 22195y 1979.
Chemical Abstracts 81, 122193h 1974.
Chemical Abstracts 81, 122263f 1974.

Primary Examiner—Mukund J. Shah
Assistant Examiner—Matthew V. Grumbling

[57] ABSTRACT

A compound contains a ligand group and at least one group of the general formula —$XR_n$ where X is a linking group which contains at least one hetero-atom, R is a saturated hydrocarbyl group containing at least six carbon atoms or is an unsaturated hydrocarbyl group containing at least three carbon atoms. The ligand group can be a polyhydroxyhydrocarbyl, a triazole, an imidazole, an indazole, a thiazole, an oxazole, a carbamate, an xanthate or a phthalazine. The compounds can be used to improve bonding between a metal and a coating material in contact with the metal surface. The metal may be a tire cord and the coating material rubber or a rubber composition.

4 Claims, No Drawings

TRIAZOLE/THIAZOLE AMINO-S-TRIAZINE BONDING AGENTS

This is a divisional of co-pending application Ser. No. 07/301,785 filed on Jan. 25, 1989 now U.S. Pat. No. 4,978,756.

The present invention relates to new compounds and the use of such compounds for the treatment of metal, more specifically for use in contact with the surface of a metal to provide improved corrosion resistance, or improved bonding, or both.

It is known to apply chemicals or mixtures of chemicals to the surface of metals in order to improve the corrosion resistance of such metals. Processes for improving the corrosion resistance of metals have been extensively described, inter alia in European Patent Applications Publication Nos. 126030 and 134699 and British Patent Specification No. 2104107.

It is also known to apply chemicals or mixtures of chemicals to the surface of metals to improve the adhesion of a surface composition to the surface of the metal. In particular, it is known to apply a coating to a metal surface which improves the strength of an adhesive bond when an adhesive composition is applied to the coated metal surface. Compounds which can be used to give improved adhesion are typically called adhesion promoters. Such compounds can be used to improve bonding in production of composite articles or in the production of printed circuit boards. An effective class of adhesion promoter for bonding of copper substrates is disclosed in U.S. Pat. No. 3,837,964. Other adhesion promoters are disclosed in U.S. Pat. Nos. 4,428,987 and 4,448,847. Organosilanes can be used as adhesion promoters, such as, for example gamma-glycidoxypropyl-trimethoxysilane and other silanes containing a functional substituent.

Good adhesion between rubber and metal is of considerable importance in rubber articles which contain metal reinforcement. A wide range of rubber articles have metal reinforcement, for example power transmission belts, conveyor belts and rubber hoses. Probably the best known use of metal reinforcement of rubber is in tires, many of which are now reinforced with metal tire cords where the metal is either steel or brass-coated steel. Many compounds have been proposed to improve the adhesion between rubber and metals which can be used as reinforcement. Substituted s-triazine compounds, and their use in bonding metal to rubber, are described in GB 1419631, GB 1419632 and GB 1504375. The use of a range of imidazolidinone compounds to form a strong adhesive bond between a vulcanised rubber and a metal reinforcing member is described in U.S. Pat. No. 4,284,536 and U.S. Pat. No. 4,300,973. The use of various compounds containing an aromatic residue such as, inter alia, 3-amino-2-carboxy-4-chlorobenzophenone to provide improved adhesion between rubber and brass is disclosed in EP 0137987. The use of an aromatic triazole to improve the adhesion of rubber to a brass-coated steel tire cord is described in GB 2032807, U.S. Pat. No. 4,169,112 and U.S. Pat. No. 4,283,460. In many cases the compound used to promote adhesion is incorporated into a rubber formulation containing conventional additives such as, for example, filler, curing agent and cure accelerator. However, U.S. Pat. No. 4,283,460 discloses adding the adhesion promoter to the rubber adjacent to the tire cord. U.S. Pat. No. 4,299,640 and GB 2037617 disclose processes in which the tire cord is coated with at least one adhesion promoter before being combined with the vulcanisable rubber composition.

We have now found a class of compound, the members of which have properties which are particularly useful in systems in which a metal is in contact with rubber.

According to the present invention there is provided a compound which contains a ligand group and a group of the formula $$-XR_n$$

where

X is a linking group which contains at least one hetero-atom;

R is a hydrocarbyl group which is either a saturated hydrocarbyl group containing at least six carbon atoms or an unsaturated hydrocarbyl group having a chain length of at least three carbon atoms; and n is an integer which has a value of at least one.

The valency of the group X is equal to $(n+1)$, and hence is at least two. Typically the value of n is one up to four and hence the valency of X is typically two up to five. The hetero-atom in the group X is a connecting atom between the group R and the ligand group and is any atom other than a carbon or hydrogen atom. The group X may be only the hetero-atom or may contain at least one atom other than the hetero-atom. Typically, the group X contains more than the hetero-atom and may contain several hetero-atoms. The hetero-atom which is present in the group X may be any hetero-atom of the type which is to be found in an organic compound and may be a sulphur atom but typically is a nitrogen or oxygen atom. The nitrogen may be present as a group $-NR^1-$ where $R^1$ is a hydrogen atom or a hydrocarbyl group, typically a lower alkyl group, that is one containing not more than five carbon atoms. The group X may be a group $-NR^1-$, but in general is a group $-COO-$ or $-NR^1CO$ or a more complex group which contains more than one hetero-atom as a connecting atom between the group R and the ligand group. Complex groups which can form the group X include groups in which two or more hetero-atoms, for example nitrogen atoms, are linked by connecting atoms which may be a straight or branched chain or a ring system. Complex groups of this type typically include a ring system which is either a hydrocarbon ring or a heterocyclic ring particularly a heterocyclic ring in which at least one of the hetero-atoms is a nitrogen atom. If the group X contains a hydrocarbon ring this may be an aromatic ring, for example a 1,4-phenylene group as in a $-NH-C_6H_4-NHCO-$ group. Heterocyclic rings which may be present in the group X include pyridine, pyrazine, pyrimidine, and triazine rings, and these heterocyclic rings may contain two or more hetero-atom substituent groups. Thus, the group X may be derived from a substituted triazine compound wherein the substituent groups each contain at least one hetero-atom, for example as in triaminotriazine. If the group X is derived from triaminotriazine, one of the amine groups is connected to the ligand group and one or both of the remaining amine groups is connected to one or more of the groups R. Thus, if the group X is derived from a triaminotriazine group, there may be up to four groups R connected to the group X, for example as in the groups $-NH-TAZ(NR_2)_2$ and $-N-$ H—TAZ(NHR)₂ where TAZ represents a triazine ring, particularly a 1,3,5-triazine ring.

The group R is a hydrocarbyl group and may be saturated or unsaturated. If the group R is a saturated hydrocarbyl group, preferably it is a group having a chain length of at least six carbon atoms. The group R may be a straight chain or branched group and is conveniently a straight chain group. The group R contains at least three or six carbon atoms depending on whether it is an unsaturated or saturated group respectively. In general the group R contains not more than 30 carbon atoms, typically not more than 24 carbon atoms, for example up to 18 carbon atoms. If the group R is a saturated hydrocarbyl group it typically contains at least 8 carbon atoms. If the group R is an unsaturated hydrocarbyl group, there may be more than one unsaturated bond present. The unsaturated bond is preferably a double bond. If the group R contains two or more double bonds, the double bonds may be conjugated or non-conjugated or, if there are sufficient double bonds, there may be a combination of both conjugated or non-conjugated double bonds present in the group R. Typically the group R, when unsaturated, contains one or two double bonds. If the group R is an unsaturated hydrocarbyl group, it is typically of the general type

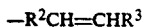
—R²CH=CHR³ where
R² is a divalent hydrocarbyl group; and
R³ is a hydrogen atom or a monovalent hydrocarbyl group.

The group R² contains at least one carbon atom and may be a methylene (—CH₂—) group or may be a saturated or unsaturated group containing at least two carbon atoms such as, for example, a heptylene group (—C₇H₁₄—), an octylene group (—C₈H₁₆—), a vinylene group (—CH=CH—), a propylene group (—CH₂—CH=CH—) or a dec-2-enylene group (—C₇H₁₄CH=CHCH₂—). The group R³ may be a hydrogen atom or a monovalent hydrocarbyl group, particularly an alkyl group containing up to ten carbon atoms, for example a methyl, pentyl, octyl or decyl group. Examples of the group R include octyl, octadecyl, allyl, decenyl, heptadecenyl, penta-1,3-dienyl, hexa-2,4-dienyl and heptadeca-8,11-dienyl groups.

The ligand group preferably contains at least two hetero-atoms. The hetero-atom can be, for example, a nitrogen, sulphur or oxygen atom. Many suitable ligand groups contain at least one of the hetero-atoms in a ring system. The ligand group may be a triazole, an imidazole, an indazole, a thiazole, an oxazole, a carbamate, a xanthate or a phthalazine group or a derivative thereof. Derivatives of the ligand group include benzotriazole, naphthotriazole, benzimidazole, naphthimidazole, 2-mercaptothiazole, 2-mercaptobenzothiazole, 2-mercaptobenzimidazole, 2-mercaptobenzoxazole and carbamate derivatives such as dithiocarbamates. The ligand group may be a substituted triazine group such as 1,3,5-triazine-2,4-dithiol. An alternative ligand group is a trihydroxybenzene group, particularly a 1,2,3-trihydroxybenzene group.

It will be appreciated that the group —X(R)ₙ is separate from the ligand group and together the two groups form the compounds of the present invention. The group —X(R)ₙ may be bonded to one of the hetero-atoms of the ligand group, but is preferably bonded to a carbon atom of the ligand group. Preferred compounds for use in the process of the present invention are those in which the ligand group is a part of a fused ring system, for example as in benzotriazole, mercaptobenzothiazole and the like, and the group —X(R)ₙ is bonded to one of the carbon atoms of the benzo group, for example as in a 5-substituted benzotriazole, a 4-substituted naphthotriazole or a 6-substituted-2-mercaptobenzothiazole.

In the compounds of the present invention the group, or groups, R is linked to the ligand group through the group X which may be, or may include, an amino, an amido, or a carbonyloxy (ester) group or a heterocyclic ring such as is present in a triazinyl group.

Compounds in which R is linked to the ligand group through an amido group (—NHCO—) include
5(hexa-2,4-dienoylamino)-benzotriazole;
6(hexa-2,4-dienoylamino)-2-mercaptobenzothiazole;
5(octadeca-9,12-dienoylamino)-benzotriazole;
6(octadeca-9,12-dienoylamino)-2-mercaptobenzothiazole;
5(octadec-9-enoylamino)-benzotriazole;
6(octadec-9-enoylamino)-2-mercaptobenzothiazole;
5(undec-10-enoylamino)-benzotriazole; and
6(undec-10-enoylamino)-2-mercaptobenzothiazole.

Compounds in which R groups are linked to the ligand group through a heterocyclic ring include those in which the ring is a triazine ring as in an aminotriazinyl group. Compounds in which the linking group is an aminotriazinyl group contain groups such as —NH—TAZ(NHR)₂ and —NH—TAZ(NR₂)₂ and include
5(2,4-bis(allylamino)-s-triazin-6-ylamino)-benzotriazole;
6(2,4-bis(allylamino)-s-triazin-6-ylamino)-2-mercaptobenzothiazole;
6(2,4-bis(diallylamino)-s-triazin-6-ylamino)-2-mercaptobenzothiazole;
5(2,4-bis(diallylamino)-s-triazin-6-ylamino)-benzotriazole;
5(2,4-bis(n-octadecylamino)-s-triazin-6-ylamino)-benzotriazole;
5(2,4-bis(di-n-octylamino)-s-triazin-6-ylamino)-benzotriazole;
6(2,4-bis(di-n-octylamino)-s-triazin-6-ylamino)-2-mercaptobenzothiazole.

Compounds in which R is linked to the ligand group through a carbonyloxy (ester) group include
5-allyloxycarbonylbenzotriazole;
3,4,5-trihydroxyallylbenzoate; and
3,4,5-trihydroxy(hexa-2,4-dien-1-yl)benzoate.

Other compounds in accordance with the present invention in which the group linking R to the ligand group is different from the linking group in the foregoing compounds include
2,4-dithiol-6(4-(hexa-2,4-dienoylamino)phenyl)amino-s-triazine
in which the ligand group is the 2,4-dithiol-s-triazine group and the linking group is a 4-amidoanilino group.

The compounds of the present invention can be prepared by the use of known reaction processes and reaction conditions. The appropriate process and conditions required depend on the type of compound being prepared, in particular the nature of the linking group X, and may also depend on the nature, and amounts, of the group R. Thus, it has been found that in the preparation of analogous compounds in one of which the group R has a longer hydrocarbon chain, the preparation of the compound in which R has a longer hydrocarbon chain may require the use of a higher reaction temperature but a higher temperature is not always necessary.

The compounds of the present invention may be prepared using, for example, amine, carboxylic acid, hydroxy, hydroxyalkyl, thiol or alkylthiol derivatives of the ligand group. The compounds of the present invention are conveniently prepared using an amine or carboxylic acid derivative of the ligand group, for example 5-aminobenzotriazole, 6-amino-2-mercaptobenzo-thiazole, 5-carboxybenzotriazole or 3,4,5-trihydroxybenzoic acid. The ligand derivative may be reacted under suitable conditions with an acid, acid chloride, alcohol, thiol or amine containing the group R to form the linking group X, for example an amido or ester link.

If the linking group is more complex, for example one including a triazine group, the compound of the present invention may be prepared by a two stage process in which the ligand derivative is reacted with a bridging compound and the intermediate product is then reacted with a suitable compound containing at least one R group, for example an amine of the type $RNH_2$ or $R_2NH$. The bridging compound is a compound containing at least two substituents, one of which is reactive with the ligand derivative and at least one of which is reactive with the compound containing at least one R group. Cyanuric chloride can be used as the bridging compound to obtain a compound in which the linking group contains a triazine group.

Compounds of the present invention in which the linking group is an amido group (—NHCO—) are conveniently prepared by the reaction of an amino-substituted derivative of the ligand group with an acid chloride of the type RCOCl. The reaction is conveniently effected in a polar solvent such as aqueous acetone. The reaction is typically effected in the presence of a base, for example sodium bicarbonate, sodium acetate or sodium hydroxide. In general this reaction can be effected without heating and it may be preferred to cool the reaction mixture to effect the reaction at a temperature which is typically in the range from 0° to 20° C.

Compounds of the present invention in which the linking group is an ester, that is carbonyloxy, group (—COO—) are conveniently prepared by the reaction of a carboxylic acid derivative of the ligand group with an alcohol of the type ROH. Other procedures for the preparation of esters may be used but the reaction between an acid and an alcohol is a particularly convenient procedure. The process for the preparation of such compounds is an esterification process and is effected under known esterification conditions. Thus, the esterification process is typically effected at an elevated temperature which is typically at least 40° C. and may be as high as 300° C. In general esterification temperatures in excess of about 150° C. are required only for the preparation of compounds of high molecular weight, particularly for the preparation of some polyesters, that is compounds containing at least two ester groups. Generally a reaction temperature of at least 60° C. is desired, for example a temperature in the range from 80° C. to 120° C. The reaction is conveniently effected in the liquid phase and may be effected using an excess of one of the reactants, particularly an excess of the alcohol, as the solvent for the reaction. We have found that if the alcohol is a dienol, for example hexa-2,4-dien-1-ol, polymerisation of the dienyl group may occur under the esterification conditions to form a polymeric material.

Thus, according to a further aspect of the present invention there is provided a polymeric material which is the product of esterifying a carboxylic acid with an alcohol which is, or an alcohol mixture which includes, a dienol. More specifically, the polymeric material is the product of esterifying a carboxylic acid with a stoichiometric excess of a dienol.

According to a specific embodiment of this further aspect of the present invention the polymeric material is the product of esterifying 3,4,5-trihydroxybenzoic acid with a stoichiometric excess of a dienol such as, for example hexa-2,4-dien-1-ol. The product obtained is essentially free of carboxylic acid groups and is believed to be a polymer of 3,4,5-trihydroxy(hexa-2,4-dien-1-yl) benzoate and hexa-2,4-dien-1-ol.

The esterification is effected under conventional esterification conditions including the presence of a catalyst such as, for example, toluene-4-sulphonyl chloride, toluene-4-sulphonic acid and concentrated sulphuric acid. We have obtained satisfactory products using toluene-4-sulphonic acid as the esterification catalyst.

Compounds in which the linking group X is more complex than amido or ester groups include compounds containing more than one group R and in which the group X is more than a divalent group. In such compounds the group X may be, for example, a substituted triazine group, more particularly a triazine group containing more than one substituent group containing a hetero-atom especially as in a polyaminotriazine group. As noted previously herein, such compounds are typically prepared in at least two stages in the first of which a ligand compound having at least one substituent containing a hetero-atom is reacted with a bridging compound which conveniently is cyanuric chloride, and the reaction product is then reacted with a compound containing at least one group R, for example a compound containing a replaceable hydrogen atom, a hetero-atom and at least one group R, such as an amine compound of the type $RNH_2$ or $R_2NH$.

The reaction of the hetero-group substituted ligand with cyanuric chloride may be effected in solution in a suitable solvent for example a polar solvent such as acetone or aqueous acetone. The reaction is typically effected in the presence of a base such as sodium bicarbonate. The reaction can be effected without the application of heat and it is generally preferred that the reaction mixture is cooled to maintain the temperature below ambient temperature and particularly to maintain a temperature of not more than 10° C., for example at 0° to 5° C.

The product obtained by the foregoing reaction is an intermediate product which contains a dichlorotriazine group linked to the ligand group through a hetero-atom, for example as in a dichlorotriazine amino substituted derivative of the ligand group. The intermediate product is then reacted with an appropriate compound such as an amine to obtain a compound in accordance with the present invention. If this subsequent reaction is effected using an amine, it is conveniently effected in the absence of a solvent using a stoichiometric excess of the amine as the reaction medium. The reaction may, if desired, be effected in the presence of a suitable inert solvent such as, for example acetone or butanone, but the presence of a solvent is not necessary. If the amine, or other reactant, is one containing an unsaturated group, a phenol is preferably present in the reaction mixture to act as a polymerisation inhibitor. A suitable phenol is 2,4,6-tri-t-butylphenol. The reaction with the amine may be effected at any suitable temperature which may be from 0° C. up to about 120° C., depending particularly on the amine used. Thus, using a lower amine, for example allylamine or diallylamine, the reaction may be effected at a temperature of not more than about 40° C., for example by cooling the reaction mixture to prevent an undesirably high temperature from being attained. Using a higher amine, for example di-n-octylamine or n-octadecylamine, a higher reaction temperature of at least 60° C. is desirable.

If the linking group is an amidoanilino group for example as in 2,4-dithiol-6(4(hex-2,4-dienoylamino)-phenyl)amino-s-triazine, the preparation of this may require three reaction stages. Thus, the compound containing the ligand group may be reacted with nitroaniline, the nitro group in the resulting compound reduced to an amine group and this reacted with an acid halide to obtain the desired product.

More specifically, nitroaniline is reacted with cyanuric chloride in essentially equimolar proportions to form 2,4-dichloro-6-(4-nitrophenyl)amino-s-triazine. The reaction is conveniently effected in a polar liquid medium which is a solvent or dispersing medium for the reactants and the reaction product, a suitable liquid medium being aqueous acetone. The reaction is preferably effected at a temperature below ambient temperature, for example from 0° C. up to 20° C., typically less than 5° C. The reaction mixture is maintained essentially neutral by the addition of a base, for example sodium carbonate, during the reaction.

The intermediate product obtained is then reacted with sodium hydrogen sulphide. The reaction is conveniently effected in water and is effected at an elevated temperature which is at least 60° C. up to 120° C. and is conveniently at the reflux temperature of the reaction mixture. Under the reaction conditions, the chlorine is replaced by thiol groups (—SH) and the nitro group is reduced to give an amino group.

The second intermediate product thus obtained is the ligand derivative which is then reacted with an acid chloride to obtain the desired product. The reaction of this ligand derivative with the acid chloride is conveniently effected using reaction conditions similar to those described previously herein for the preparation of compounds in which the linking group X is an amido group.

The compounds of the present invention, and any intermediate materials if desired, may be purified using appropriate techniques known for this purpose such as extraction with suitable liquids which are solvents either for the desired product or impurities. The product may be crystallised from suitable solvents or may be thoroughly washed using one or more liquids to remove undesired impurities.

The compounds of the present invention are effective to reduce corrosion of metals or to improve the adhesion of a metal to another material or to both reduce corrosion and improve adhesion. The preferred compound is dependent on the nature of the ligand group, the nature of the group —$XR_n$ and the metal. Thus, if the ligand group is a benzotriazole group, the metal is preferably copper, if the ligand group is a mercapto-benzothiazole group the metal is preferably zinc and if the ligand is a 1,2,3-trihydroxyphenyl group the metal is preferably iron or steel.

The compounds of the present invention may be used in composites of a metal and a non-metallic material, for example a polymeric material such as rubber. The metal may be a reinforcement for the non-metallic material, for example rubber reinforced with a metal as in power transmission belts, conveyor belts, rubber hoses and metal reinforced tires.

Thus, a particular embodiment of the present invention comprises a composite which is metal reinforced rubber which also includes at least one compound in accordance with the first aspect of the present invention.

The composite is, in particular, in the form of a tire reinforced with metal tire cords.

When the metal reinforcement is a tire cord it is typically formed of steel or brass-coated steel.

The composite may include more than one compound in accordance with the present invention. It is preferable to use more than one compound if the metal is an alloy and the compounds then very preferably contain different ligand groups. Thus, if the metal is a brass-coated steel tire cord, there may be present three different compounds in each of which there is a different ligand group, particularly compounds in which the ligand groups are benzotriazole, mercaptobenzothiazole and 1,2,3-trihydroxybenzene. The compounds are used in proportions depending on the composition of the brass coating and also the completeness of coating of the steel cord. A typical mixture of compounds would be such as to provide from 5 up to 95%, especially 30–60%, molar of benzotriazole ligand groups, from 5 up to 95%, especially 30–60%, molar of mercaptobenzothiazole ligand groups and from 1 up to 90%, especially 5–30%, molar of 1,2,3-trihydroxybenzene ligand groups, the % molar of ligand groups totalling 100%.

The rubber may be natural or synthetic rubber and may be formulated with various additives of the type known in the rubber compounding art.

As noted previously herein, the preferred compound is dependent on the nature of the group —$XR_n$. When used in metal reinforced rubber, it is preferred that the group R is an unsaturated hydrocarbyl group. We have found that better effects are generally obtained when the group R contains not more than 12 carbon atoms. If the group X is a group —COO— or —NHCO—, the group R may be an unsaturated group containing 3 to 12 carbon atoms and the value of n is one whereas if X is an amino-substituted triazine group, the group R is conveniently an unsaturated group containing 3 to 6 carbon atoms and the value of n is at least two and may be four.

If the metal is brass-coated steel, when using a single compound we have obtained particularly useful results using compounds in which the ligand group is a 2-mercaptobenzothiazole group.

A particularly useful type of compound in accordance with the present invention is one in which the ligand group is mercaptobenzothiazole, especially 2-mercaptobenzothiazole, the group X is —COO— or —NHCO—, or an amino-substituted triazine, the group R is an unsaturated group containing 3 to 12 carbon atoms and the value of n is one when X is —COO— or —NHCO— and the value of n is at least two up to four when X is an amino-substituted triazine group. Compounds of the foregoing type include 6(hexa-2,4-dienoylamino)-2-mercaptobenzothiazole;
6(undec-10-enoylamino)-2-mercaptobenzothiazole;
6(2,4-bis(allylamino)-s-triazine-6-ylamino)-2-mercaptobenzothiazole; and
6(2,4-bis(diallylamino)-s-triazine-6-ylamino)-2-mercaptobenzothiazole.

Especially useful results have been obtained using compounds in which the group X is an amino-substituted triazine group.

The compounds of the present invention may be incorporated into the rubber formulation, for example as is disclosed in GB 2032807, U.S. Pat. No. 4,169,112 and U.S. Pat. No. 4,283,460. Alternatively, the compounds of the present invention may be incorporated only into a part of the rubber formulation, this part of the rubber formulation being that adjacent to the metal, as is disclosed in U.S. Pat. No. 4,283,460. As a yet further alternative, the compounds of the present invention may be applied to the metal, as is disclosed in U.S. Pat. No. 4,299,640 and GB 2037617. It will be appreciated that the foregoing procedures may be combined and one or more compounds in accordance with the present invention may be applied to the metal and one or more compounds in accordance with the present invention incorporated into the rubber which is to be applied to the metal, and the compound, or compounds, on the metal and in the rubber may be the same or different.

In order that the various embodiments of the present invention are more readily appreciated, various aspects thereof are described in the following, non-limiting examples in which parts are by weight unless specified to the contrary.

EXAMPLE 1

(A) Preparation of hexa-2,4-dienoyl chloride 11.2 parts of hexa-2,4-dienoic acid (sorbic acid, obtained from Aldrich Chemical Co. Ltd.) were stirred with 60 parts of toluene containing 1 part of dimethylformamide and 0.2 parts of 2,4,6-tri-t-butylphenol. The mixture was heated to 75° C. Complete solution was observed when the temperature reached 40° C. A solution containing 13.5 parts of thionyl chloride dissolved in 30 parts of toluene was then added dropwise to the hot solution of hexa-2,4-dienoic acid over a period of 1.5 hours, maintaining the internal temperature at 75°-80° C. A pale brown solution was obtained and this was stirred for a further one hour. The toluene was then removed by distillation under reduced pressure. (20-25 Torr), and a temperature of 65°-70° C. Distillation was continued at 15-18 Torr, and 80°-82° C. 9.0 parts (69% yield based on the acid) of a pale yellow distillate were collected.

By analysis the product was found to contain C 55.1% wt %; H 5.4% wt; and Cl 27.1% wt. Hexa-2,4-dienoyl chloride ($C_6H_7ClO$) requires C 55.2% wt; H 5.36% wt; and Cl 27.2% wt.

(B) Preparation of 5(hexa-2,4-dienoylamino)benzotriazole

A mixture of 2.68 parts of 5-aminobenzotriazole, prepared as described in U.S. Pat. No. 4,428,987, 25 parts of water and 100 parts of acetone was warmed to 40° C. to effect a complete solution. To this solution was then added a suspension containing 2.5 parts of sodium bicarbonate in 20 parts of water. The resulting mixture was stirred and cooled to 5°-10° C. in a cooling bath containing ice and water. A solution containing 3.0 parts of hexa-2,4-dienoyl chloride (prepared as described in A) dissolved in 20 parts of acetone was added dropwise to the reaction mixture over 30 minutes, maintaining an internal temperature of between 5° and 10° C. throughout the addition. A further charge of 1.5 parts of hexa-2,4-dienoyl chloride dissolved in 10 parts of acetone was added over 15 minutes, and stirring was continued at between 5° and 10° C. for one hour. A solution containing 5 parts of sodium bicarbonate dissolved in 150 parts of water was then added, and the reaction mixture stirred for two hours, allowing the internal temperature to rise to between 20° and 25° C. A pale cream solid (2.75 parts, melting point 215°-217° C., 58.3% yield) was isolated by filtration, washed with water and dried at reduced pressure (18-22 Torr) at 20° C. for 24 hours.

By analysis the product was found to contain C 61.0% wt; H 5.2% wt; N 23.6% wt. The compound 5(hexa-2,4-dienoylamino)benzotriazole ($C_{12}H_{12}N_4O$) requires C 63.2% wt; H 5.3% wt; N 24.6% wt.

EXAMPLE 2

(A) Preparation of 6-amino-2-mercaptobenzothiazole

A solution containing 100 parts of 2-mercaptobenzothiazole dissolved in 146 parts of concentrated sulphuric acid (SG 1.84) was cooled to 0°-2° C. The solution was treated with a mixture of 37 parts of fuming nitric acid (SG 1.5) and 30 parts of sulphuric acid (SG 1.84) over 3.5 hours, maintaining the internal temperature of the mixture at 0°-5° C. The mixture was allowed to warm to 20°-25° C. and stirred for a further 16 hours. The yellow solution was then poured carefully into 1000 parts of crushed ice which was being stirred. A pale yellow precipitate was formed which was isolated by filtration and washed well with cold water. The yellow filtercake was dissolved in 1000 parts of water and sufficient 10N aqueous sodium hydroxide solution to raise the pH of the solution to between 11 and 12. This solution was filtered and acidified, with stirring, to a pH in the range 2 to 3 by the addition of concentrated hydrochloric acid. A bright yellow precipitate (113 parts) was formed which was isolated by filtration and dried at 60° C. for 48 hours.

132 Parts of sodium hydrogen sulphide was dissolved in 400 parts of water, and stirred at 20° C. 53 Parts of 6-nitro-2-mercaptobenzothiazole, prepared as described previously herein, was added over 10 minutes; the reaction mixture was then heated to 110° C., and stirred whilst boiling the mixture under reflux conditions. After four hours boiling, the mixture was cooled to between 0° and 5° C. and stirred for one hour. The product, 6-amino-2-mercaptobenzothiazole (30.3 parts), was isolated by filtration, washed sparingly with cold water and dried at 60° C. for 24 hours.

(B) Preparation of 6(hexa-2,4-dienoylamino)-2-mercaptobenzothiazole 3.60 Parts of 6-amino-2-mercaptobenzothiazole (prepared as described in A) were reacted with hexa-2,4-dienoyl chloride (prepared as described in part A of Example 1) using the procedure described in part B of Example 1.

By analysis, the product obtained (1.45 parts, melting point 264°-266° C., 26% yield) was found to contain C 55.8% wt; H 4.4% wt; N 9.7% wt; and S 22.0% wt. 6(hexa-2,4-dienoylamino)-2-mercaptobenzothiazole ($C_{13}H_{12}N_2S_2O$) requires C 56.5% wt; H 4.3% wt; N 10.1% wt; and S 23.7% wt.

EXAMPLE 3

(A) Preparation of Octadeca-9,12-dienoyl chloride 27.5 Parts of octadeca-9,12-dienoic acid (linoleic acid) were stirred with 50 parts of toluene and 0.5 parts of dimethyl formamide. The solution was heated to 75° C. and 15 parts of thionyl chloride dissolved in 50 parts of toluene were added slowly over 1.5 hours whilst maintaining the reaction temperature at 75°-80° C. After a further 2.5 hours, the toluene was removed by distillation under reduced pressure (20-25 Torr) and a temperature of 70°-80° C. and then the product (20.0 parts; 67.9% yield) was obtained by distillation at 0.1 Torr and a temperature of 160°–170° C.

By analysis the product was found to contain C 72.0% wt; H 10.3% wt; and Cl 11.8% wt. Octadeca-9,12-dienoyl chloride ($C_{18}H_{31}ClO$) requires C 72.4% wt; H 10.4% wt; and Cl 11.9% wt.

(B) Preparation of 5(octadeca-9,12-dienoylamino)-benzotriazole 13.4 Parts of 5-aminobenzotriazole, prepared as described in U.S. Pat. No. 4,428,987, 200 parts of water, 10 parts of sodium bicarbonate and 100 parts of acetone were stirred together and cooled to 5° C. by immersion in an ice-bath.

A solution containing 39 parts of octadeca-9,12-dienoyl chloride (prepared as described in A) and 30 parts of acetone was added to the stirred reaction mixture over one hour, maintaining the temperature below 10° C. throughout the addition. After stirring for a further three hours whilst allowing the temperature to rise to 20° C., 15 parts of 10N aqueous sodium hydroxide were added, and the mixture was stirred at 20° C. for 16 hours. 10 Parts of glacial acetic acid were then added, and the reaction mixture was filtered. The collected solid was washed well with water (about 20° C.) and dried at 60° C. for 16 hours. A slightly sticky solid was obtained and this was stirred in 200 parts of chloroform at 20° C. for 5 hours. The solid product (18.3 parts, melting point 169°–171° C., 46.2% yield) was isolated by filtration, washed with chloroform, and dried at 60° C. for 16 hours.

By analysis the product was found to contain C 70.3% wt; H 9.3% wt; and N 13.4% wt. 5(octadeca-9,12-dienoylamino)benzotriazole ($C_{24}H_{36}ON_4$) requires C 72.7% wt; H 9.1% wt; and N 14.1% wt.

EXAMPLE 4

Preparation of 6(octadeca-9,12-dienoylamino)-2-mercaptobenzothiazole 3.6 Parts of 6-amino-2-mercaptobenzothiazole (prepared as described in Part A of Example 2) were stirred with 200 parts of acetone and 50 parts of water. A solution containing 3.2 parts of anhydrous sodium acetate dissolved in 30 parts of water was added, and the mixture cooled to between 10° and 15° C. 8 Parts of octadeca-9,12-dienoyl chloride (prepared as described in Part A of Example 3), dissolved in 50 parts of acetone was added to the stirred reaction mixture over one hour whilst maintaining the internal temperature at between 10° and 15° C. by immersion in a bath containing ice and water. The reaction mixture was stirred for a further four hours at less than 15° C., then 10 parts of a 10N aqueous solution of sodium hydroxide were added, and the mixture was stirred for 16 hours, allowing the temperature to rise to 20° C.

7 Parts of glacial acetic acid were then added, and the mixture was filtered. The collected solid was washed with water and dried at 18–25 Torr and 20° C. for 24 hours.

The product (5.22 parts, melting point 158°–160° C., 55.8% yield) was found by analysis to contain C 64.2% wt; H 8.0% wt; N 5.8% wt; and S 13.5% wt. 6(Octadeca-9,12-dienoylamino)-2-mercaptobenzothiazole ($C_{25}H_{36}N_2S_2O$) requires C 67.6% wt; H 8.1% wt; N 6.3% wt; and S 14.4% wt.

EXAMPLE 5

(A) Preparation of Octadec-9-enoyl chloride

Octadec-9-enoyl chloride (25.5 parts, boiling point 160°–180° C. at 0.12 Torr, 85% yield) was prepared from 28.1 parts of octadec-9-enoic acid using the procedure described in part A of Example 3 for the preparation of octadec-9,12-dienoyl chloride.

(B) Preparation of 5(octadec-9-enoylamino)benzotriazole 2.68 Parts of 5-aminobenzotriazole (prepared as described in U.S. Pat. No. 4,428,987) were reacted with 7.0 parts of octadec-9-enoyl chloride (prepared as described in A) using the procedure described in part B of Example 3 for the preparation of 5(octadeca-9,12-dienoylamino)-benzotriazole.

The product (2.4 parts, melting point 180°–181° C., 29.6% yield) was found by analysis to contain C 70.8% wt; H 10.0% wt; and N 14.0% wt. 5(Octadec-9-enoylamino) benzotriazole ($C_{24}H_{38}N_4O$) requires C 72.4% wt; H 9.5% wt; and N 14.1% wt.

EXAMPLE 6

Preparation of 6(octadec-9-enoylamino)-2-mercaptobenzothiazole 3.6 Parts of 6-amino-2-mecrcaptobenzothiazole (prepared as described in part A of Example 2) were reacted with 7.8 parts of octadec-9-enoyl chloride (prepared as described in part A of Example 5) using the procedure described in Example 4 for the preparation of 6(octadeca-9,12-dienoylamino)-2-mercaptobenzothiazole.

The product (3.60 parts, melting point 154°–156° C., 40.8% yield) was found by analysis to contain C 66.9% wt; H 8.9% wt; N 6.1% wt; and S 14.3% wt. 6(octadec-9-enoylamino)-2-mercaptobenzothiazole ($C_{25}H_{38}N_2S_2O$) requires C 67.3% wt; H 8.5% wt; N 6.3% wt; and S 14.3% wt.

EXAMPLE 7

(A) Preparation of undec-10-enoyl chloride

Undec-10-enoyl chloride (12 parts, boiling point 80°–84° C. at 0.16 Torr, 59.25% yield) was prepared from 18.4 parts of undec-10-enoic acid (obtained from Aldrich Chemical Co. Ltd.) using the procedure described in part A of Example 3.

(B) Preparation of 5(undec-10-enoylamino)-benzotriazole 2.68 Parts of 5-aminobenzotriazole (prepared as described in U.S. Pat. No. 4,428,987) were reacted wiht 7.56 parts of undec-10-enoyl chloride (prepared as described in part A), using the procedure described in Example 4 for the preparation of 6(octadec-9,12-dienoylamino)-2-meraaptobenzothiazole.

The product (4.5 parts, melting point 189°–191° C., 73.3% yield) was found by analysis to contain C 66.5% wt; H 8.4% wt; and N 17.8% wt. 5(undec-10-enoylamino)-benzotriazole ($C_{17}H_{24}N_4O$) requires C 68% wt; H 8.0% wt; and N 18.7% wt.

EXAMPLE 8

Preparation of 6(undec-10-enoylamino)-2-mercaptobenzothiazole 3.6 Parts of 6-amino-2-mercaptobenzothiazole (prepared as described in part A of Example 2) were reacted with 5.1 parts of undec-10-enoyl chloride (prepared as described in part A of Example 7) using the procedure described in Example 4 for the preparation of 6(octadec-9,12-dienoylamino)-2-mercaptobenzothiazole.

The product (4.15 parts, melting point 140°-142° C., 58.5% yield) was found by analysis to contain C 60.8% wt; H 7.0% wt; N 7.8% wt; and S 18.4% wt. 6(undec-10-enoylamino)-2-mercaptobenzothiazole ($C_{18}H_{24}N_2S_2O$) requires C 62.1% wt; H 6.9% wt; N 8.0% wt; and S 18.4% wt.

EXAMPLE 9

(A) Preparation of 5(2,4-dichloro-s-triazin-6-ylamino)benzotriazole 21.44 Parts of 5-aminobenzotriazole (prepared as described in U.S. Pat. No. 4,428,987) and 280 parts of acetone were warmed to 40° C. to effect a complete solution. After cooling to below 10° C. this solution was added to a stirred solution containing 28.8 parts of cyanuric chloride dissolved in 200 parts of acetone. The reaction mixture was stirred at between 0° and 5° C. and a solution containing 13.6 parts of sodium bicarbonate in 200 parts of water was added dropwise over one hour whilst maintaining the internal temperature at between 0° C. and 5° C. by means of an external ice-bath. The reaction mixture was then stirred at between 0° and 5° C. for a further two hours. A pale cream solid (43.6 parts, 96% yield) was isolated by filtration, washed well with cold water, and dried at 18-25 Torr and 20° C. for 48 hours.

By analysis the product was found to contain C 38.0% wt; H 2.3% wt; N 33.7% wt; and Cl 24.3% wt. 5(2,4-dichloro-s-triazin-6-ylamino)-benzotriazole ($C_9H_5N_7Cl_2$) requires C 38.3% wt; H 1.77% wt; N 34.8% wt; and Cl 25.2% wt.

(B) Preparation of 5(2,4-bis(allylamino)-s-triazin-6-ylamino)benzotriazole

10 Parts of allylamine and 0.1 parts of 2,4,6-tri-t-butylphenol were stirred together at 20°C. 4.5 parts of 5-(2,4-dichloro-s-triazin-6-ylamino)benzotriazole (prepared as described in part A) were added in small portions over 30 minutes. The temperature was maintained at between 30° and 35° C. by cooling the reaction mixture externally in a water bath (temperature of bath 20°±2° C.). The resulting mixture was stirred at between 20° and 25° C. for 16 hours. 100 parts of cold water (20° C.) were then added, and a pale yellow solid was isolated by filtration, and washed with water. The filter cake so obtained (4.8 parts) was stirred with 150 parts of water. This mixture was treated with 1.5 parts of sodium hydroxide pellets, and stirred for ten minutes. 0.5 Parts of decolourising charcoal (Carbon DY3) were added, and stirring was continued, at 20° C., for a further 30 minutes. The mixture was filtered, and the filtrates were acidified with 3 parts of glacial acetic acid. The product (2.6 parts, melting point 100°-104° C., 49.3% yield) was isolated by filtration, washed with water and dried at 18-25 Torr and 20° C. for 24 hours.

By analysis the product was found to contain C 54.1% wt; H 5.4% wt; and N 36.5% wt. The compound 5(2,4-bis(allylamino)-s-triazin-6-ylamino)benzotriazole ($C_{15}H_{17}N_9$) requires C 55.7% wt; H 5.3% wt; and N 39% wt.

EXAMPLE 10

(A) Preparation of 6(2,4-dichloro-s-triazin-6-ylamino)-2-mercaptobenzothiazole 14.4 Parts of 6-amino-2-mercaptobenzothiazole (prepared as described in part A of Example 2) were reacted with 14.4 parts of cyanuric chloride using the procedure described in part A of Example 9.

By analysis the product obtained (22.3 parts, 70% yield) was found to contain C 34.7% wt; H 1.6% wt; N 20.0% wt; Cl 20.0% wt; and S 19.5% wt. 6(2,4-dichloro-s-triazin-6-ylamino)-2-mercaptobenzothiazole ($C_{10}H_5N_5Cl_2S_2$) requires C 36.4% wt; H 1.5% wt; N 21.2% wt; Cl 21.5% wt; and S 19.4% wt.

(B) Preparation of 6(2,4-bis(allylamino)-s-triazin-6-ylamino)-2-mercaptobenzothiazole 5.3 Parts of 6(2,4-dichloro-s-triazin-6-ylamino)-2-mercaptobenzothiazole (prepared as described in part A) were added in small portions to a stirred mixture of 10 parts of allylamine and 0.1 parts of 2,4,6-tri-t-butylphenol whilst maintaining the temperature of the reaction mixture at between 25° and 30° C. by immersion in a bath containing cold water (20°±2° C.). After stirring at 20° C. for a further 16 hours, the reaction mixture was poured into 200 parts of cold water (20° C.). An oily insoluble material was formed which was separated from the water and dissolved in 100 parts of chloroform. The chloroform solution was washed with 20 parts of an aqueous N hydrochloric acid solution, and the layers were separated. The chloroform solution was dried over anhydrous magnesium sulphate and then evaporated to dryness. A sticky solid was produced which was stirred in 100 parts of hexane for 16 hours, and the solid (2.10 parts, melting point 216°-220° C., 36.1% yield) was isolated by filtration, washed with hexane, and dried at 18-25 Torr and 20° C. for 24 hours.

By analysis this product was found to contain C 50.6% wt; H 4.7% wt; N 25.5% wt; and S 16.6% wt. 6(2,4-bis(allylamino)-s-triazin-6-ylamino)-2-mercaptobenzothiazole ($C_{16}H_{17}N_7S_2$) requires C 51.8% wt; H 4.6% wt; N 26.4% wt; and S 17.3% wt.

EXAMPLE 11

Preparation of 6(2,4-bis(diallylamino)-s-triazin-6-ylamino)-2-mercaptobenzothiazole 11 Parts of diallylamine and 0.1 parts of 2,4,6-tri-t-butylphenol were stirred at 20° C. 5.3 Parts of 6(2,4-dichloro-s-triazin-6-ylamino)-2-mercaptobenzothiazole (prepared as described in Part A of Example 10) were added in small portions over 30 minutes whilst maintaining the internal temperature at between 30° and 35° C. by application of external water cooling. The resultant mixture was stirred for 16 hours at between 20° and 25° C. 200 Parts of chloroform were then added, and the resultant dark brown solution was washed with 200 parts of dilute aqueous hydrochloric acid (0.5M) followed by further washing with 100 parts of dilute sodium chloride solution (1.0% w/v). The organic solution was then dried over anhydrous magnesium sulphate, and the chloroform then removed by evaporation. An oil was obtained and this was stirred with 100 parts of hexane for two hours. A yellow solid (1.9 parts, melting point 160°-161° C., 28.6% yield) was isolated by filtration, washed with hexane and dried at 60° C. for five hours.

By analysis the product was found to contain C 58.1% wt; H 5.5% wt; N 21.4% wt; and S 13.8% wt. 6(2,4-bis(diallylamino)-s-triazin-6-ylamino)-2-mercaptobenzothiazole ($C_{22}H_{25}N_7S_2$) requires C 58.5% wt; H 5.5% wt; N 21.7% wt; and S 14.2% wt.

EXAMPLE 12

Preparation of 5(2,4-bis(diallylamino)-s-triazin-6-ylamino)benzotriazole 4.5 Parts of 5(2,4-dichloro-s-triazin-6-ylamino)benzotriazole (prepared as described in part A of Example 9), were reacted with 12.5 parts of diallylamine using the procedure described in Example 11 for the preparation of 6(2,4-bis(diallylamino)-s-triazin-6-ylamino)-2-mercaptobenzothiazole.

The product (2.4 parts, melting point 74°–76° C., 37.4% yield) was found by analysis to contain C 61.3% wt; H 6.0% wt; and N 29.8% wt. 5(2,4-bis(diallylamino)-s-triazin-6-ylamino)benzotriazole ($C_{21}H_{25}N_9$) requires C 62.5% wt; H 6.2% wt; and N 31.3% wt.

EXAMPLE 13

Preparation of 5(2,4-bis(n-octadecylamino)-s-triazin-2-ylamino)benzotriazole 4.0 Parts of 5(2,4-dichloro-s-triazin-6-ylamino)benzotriazole (prepared as described in part A of Example 9) were added to 25 parts of n-octadecylamine, and the mixture stirred at between 80° and 90° C. for 16 hours. After cooling to 30° C., 200 parts of industrial methylated spirits were added, followed by 200 parts of hexane. 20 Parts of cupric acetate and a further 200 parts of methylated spirits were then added. After stirring at 20° C. for one hour, the reaction mixture was filtered, and the collected solid washed well with methylated spirits. The solid was then stirred with 200 parts of chloroform, and the resultant solution washed with 100 parts of N aqueous hydrochloric acid. This washing procedure was repeated three times. Finally the chloroform solution was washed with water, dried over anhydrous magnesium sulphate, and evaporated to dryness. The solid thus obtained was stirred with 50 parts of methylated spirits for one hour.

The solid (2.30 parts, melting point 84°–86° C., 21% yield) was found by analysis to contain C 70.7% wt; H 11.1% wt; and N 16.2% wt. The compound 5(2,4-di(n-octadecylamino)-s-triazin-6-ylamino)benzotriazole ($C_{45}H_{81}N_9$) requires C 72.3% wt; H 10.8% wt; and N 16.9% wt.

EXAMPLE 14

Preparation of 5(2,4-bis(di-n-octaylamino)-s-triazin-6-ylamino)benzotriazole 25 Parts of di-n-octylamine were stirred and heated to 75° C. 3.0 Parts of 5(2,4-dichloro-s-triazin-6-ylamino)-benzotriazole (prepared as described in part A of Example 9) were added quickly to the amine. The reaction mixture was stirred at between 70° and 75° C. for 12 hours, then cooled to 20° C. and poured into 300 parts of industrial methylated spirits. 10 Parts of cupric acetate were added, and the mixture stirred for one hour at 20° C. The green crystalline solid which had formed was filtered and washed with methylated spirits. The filter cake was then stirred in 200 parts of ethyl acetate, and 100 parts of aqueous 2N hydrochloric acid were added. The mixture was stirred vigorously for 20 minutes, then transferred to a suitable funnel, where the aqueous and organic layers disengaged. The lower aqueous layer was discarded, and replaced with fresh 2N aqueous hydrochloric acid, and the wash process was repeated. Finally, the ethyl acetate layer was dried over anhydrous magnesium sulphate, and then the solvent was removed at 18–22 Torr and 50°±5° C. An oily product was obtained which was recrystallised from 50 parts of boiling methanol, to produce 2.88 parts of a solid product (melting point 78°–80° C., 39.45% yield).

By analysis the product was found to contain C 71.3% wt; H 10.8% wt; and N 18.4% wt. 5(2,4-bis(di-n-octylamino)-s-triazin-6-ylamino)benzotriazole ($C_{41}H_{73}N_9$) requires C 71.2% wt;

EXAMPLE 15

Preparation of 6(2,4-bis(di-n-octylamino)-s-triazin-6-ylamino)-2-mercaptobenzothiazole 3 Parts of 6(2,4-dichloro-s-triazin-6-ylamino)-2-mercaptobenzothiazole (prepared as described in part A of Example 10) were reacted with 25 parts of di-n-octylamine using the procedure described in Example 14 for the preparation of 5(2,4-bis(di-n-octylamino)-s-triazin-6-ylamino)benzotriazole. A yield of 0.96 parts of product of melting point 81°–83° C. was obtained.

EXAMPLE 16

(A) Preparation of 5-carboxybenzotriazole 45.6 Parts of 3,4-diaminobenzoic acid (obtained from Lancaster Synthesis Ltd.) were stirred with 600 parts of water and 60 parts of concentrated aqueous hydrochloric acid of specific gravity 1.18. The reaction mixture was heated to 60° C., and filtered whilst hot. The filtrates were cooled to below 5° C. by immersing the reaction vessel in a bath containing crushed ice. 160 Parts of an aqueous 2N solution of sodium nitrite were added all at once to the cooled reaction mixture causing the internal temperature to rise to 22° C. The reaction mixture was then heated to 60° C. and stirred at 60° C. for 30 minutes. After cooling to 20° C., a solid product (46.15 parts, 94.4% yield) was isolated by filtration, washed with cold water (20° C.) and dried at 60° C. for 24 hours.

(B) Preparation of 5-allyloxycarbonyl benzotriazole 3.0 Parts of 5-carboxybenzotriazole (prepared as described in A) were added to a stirred mixture containing 50 parts of allyl alcohol and 0.2 parts of toluene-4-sulphonic acid. The reaction mixture was heated at the boil (94°–97° C.) under reflux conditions for 24 hours. 0.3 Parts of concentrated sulphuric acid were then added and heating at the boil under reflux was continued for a further 48 hours. The excess allyl alcohol was removed by distillation under reduced pressure (20–25 Torr) and at 40°–50° C. and the residual oil was dissolved in 100 parts of ethyl acetate. The ethyl acetate solution was washed with 100 parts of water, then dried over anhydrous magnesium sulphate. The ethyl acetate was then removed by distillation at 18–22 Torr and 50°±5° C., and the residual solid was stirred in 200 parts of hexane for four hours. The solid product (1.15 parts, melting point 95°–97° C., 30.8% yield) was collected by filtration, washed with hexane and dried at 20–25 Torr and 20° C. for 16 hours.

By analysis, the product was found to contain C 58.8% wt; N 20.1% wt; and H 4.6% wt. The compound 5-allyloxycarbonylbenzotriazole ($C_{10}H_9N_3O_2$) requires C 59.1% wt; N 20.7% wt; and H 4.4% wt.

EXAMPLE 17

Preparation of 3,4,5-trihydroxyallylbenzoate 13.6 Parts of 3,4,5-trihydroxybenzoic acid (gallic acid, obtained from Aldrich Chemical Company) were added to 60 parts of allyl alcohol, containing 0.5 parts of 2,4,6-tri-t-butylphenol and 0.4 parts of toluene-4-sulphonic acid. The mixture was heated at the boil (94°–97° C.) under reflux conditions for 20 hours. A further charge of 0.4 parts of toluene-4-sulphonic acid was added, and boiling under reflux conditions continued for a further 16 hours.

Excess allyl alcohol was then removed under vacuum distillation (20–25 Torr) and an internal temperature not exceeding 60° C. The residual solid was dissolved in 200 parts of ethyl acetate and washed with 100 parts of water. After separating the aqueous and organic layers, the latter was washed with three separate portions of 50 parts of an aqueous solution containing 1 part of sodium bicarbonate. After drying over anhydrous magnesium sulphate, the ethyl acetate was removed by vacuum distillation at 18–22 Torr and 50°±5° C. The crude product (11.0 parts) was recrystallised from a mixture containing 90 parts of toluene and 10 parts of ethyl acetate, to yield the final product (8.65 parts, melting point 153° C., 51.5% yield).

By analysis this product was found to contain C 57.6% wt; and H 5.0% wt. The compound 3,4,5-trihydroxyallylbenzoate ($C_{10}H_{10}O_5$) requires C 57.1% wt; and H 4.8% wt.

EXAMPLE 18

10 Parts of 3,4,5-trihydroxybenzoic acid (obtained from Aldrich Chemical Company) was added to a stirred mixture containing 35 parts of hexa-2,4-dien-1-ol (also obtained from Aldrich Chemical Company) and 0.5 parts of toluene-4-sulphonic acid. The mixture obtained was stirred at between 90° and 100° C. for 24 hours. A viscous dark brown liquid was obtained which did not contain any 3,4,5-trihydroxybenzoic acid, as evaluated by comparative thin layer chromatography. This viscous liquid was dissolved in 200 parts of acetone and 200 parts of isopropanol. 10 Parts of this solution were evaporated to dryness, to give 1.0 part of a light brown solid.

By analysis this compound was found to contain C 74.7% wt; and H 8.5% wt.

EXAMPLE 19

Preparation of 2,4-dithio-6(4-(hexa-2,4-dienoylamino)phenyl)amino-s-triazine

A solution containing 13.8 parts of 4-nitroaniline (obtained from Aldrich Chemical Company) dissolved in 160 parts of acetone and 20 parts of water was added dropwise, over 30 minutes, to a stirred suspension of 18.6 parts of cyanuric chloride, 240 parts of acetone and 200 parts of crushed ice. The temperature was maintained at less than 5° C. by immersing the reaction vessel in a bath containing crushed ice and water. The pH of the mixture was maintained at between 6 and 7 by the dropwise addition of 53 parts of aqueous 2N sodium carbonate solution. After stirring for a further three hours at below 5° C., the reaction mixture was filtered, and the filter cake washed well with cold water (20° C.). The filter cake was stirred with 300 parts of water, and a suspension containing 328 parts of sodium hydrogen sulphide partially dissolved in 600 parts of water was added. This mixture was heated at the boil (about 100° C.) under reflux conditions for 16 hours. After cooling to 20° C., the reaction mixture was neutralised by the addition of 300 parts of glacial acetic acid. A grey solid was formed which was collected by filtration and washed with cold water (20° C.). The solid was then stirred with 600 parts of aqueous N sodium carbonate solution, heated to 60° C., and stirred for 30 minutes at 60° C. The solution so formed was filtered hot, cooled to 15° C. and 40 parts of glacial acetic acid were added slowly over one hour.

A solid (10.45 parts, 34.9% yield) was precipitated and this was isolated by filtration, washed with water and dried at 60° C. for 24 hours.

By analysis the product was found to contain C 36.1% H 3.2% wt; N 23.0% wt; and S 22.8% wt. 2,4-Dithio-6(4-aminophenyl)amino-s-triazine ($C_9H_9N_5S_2$) requires C 43.0% wt; H 3.6% wt; N 27.9% wt; and S 25.5% wt.

5 Parts of 2,4-dithio-6(4-aminophenyl)-amino-s-triazine, (prepared as described previously) were stirred with 200 parts of dimethylformamide and 200 parts of acetone. The mixture was cooled to between 5° and 10° C. by immersion in a cooling bath containing ice and water. A solution of 3.5 parts of hexa-2,4-dienoyl chloride (prepared as described in part A of Example 1) dissolved in 10 parts of acetone, was added dropwise to the stirred reaction mixture over 30 minutes, maintaining the internal temperature at between 5 and 10° C., and the pH of the mixture at between 5 and 6 by dropwise addition of 10 parts of aqueous 2N sodium carbonate solution. After stirring for one hour, 5 parts of aqueous 10N sodium hydroxide were added, and the reaction mixture stirred for 16 hours whilst allowing the temperature to rise to 20° C. 5 Parts of glacial acetic acid were then added, and the mixture was poured into 700 parts of water. The product (4.52 parts, 74.7% yield) was isolated by filtration, washed with water, dried at 60° C. for 24 hours, stirred with 200 parts of chloroform for four hours at 20° C., filtered, washed with chloroform and dried at 60° C. for three hours.

By analysis the product was found to contain C 49.6% wt; H 4.8% wt; and N 19.5% wt. The compound 2,4-dithio-6(4-(hexa-2,4dienoylamino)phenyl)-amino-s-triazine ($C_{15}H_{15}ON_5S_5$) requires C 52.2% wt; H 4.3% wt; and N 20.3% wt.

EXAMPLES 20 to 48

Samples of brass-coated steel wire, of the type used in reinforced car and truck tyres, were cut into 10 cm lengths and degreased by immersion in 1,1,2,2-tetrachloroethylene at 120°C. The degreased wire samples were immersed in 0.5% w/v solutions of products of Examples 1 to 19 or of mixtures of products of Examples 1 to 19, the concentration of the mixture being 0.5% w/v. The solvent employed depended on the product or mixture, and is indicated in Table One. After 30–40 seconds immersion the samples were removed from the solutions and dried in a stream of cold air. The treated samples, together with several untreated wire samples, were subjected to a corrosion test as set out hereafter.

Before being subjected to this corrosion test, one end of each wire sample was immersed, to approx. 0.2 cm length, in butyl rubber paint for 5–10 seconds. The paint was allowed to dry for an hour at 20° C. The wire samples so treated were then subjected to a corrosion test by immersing in distilled water at 20° C., ensuring that the rubber-treated end of the cord was submerged, and the unpainted end of the cord protruded above the surface of the water. After 20 hours, the cords were removed from the water and allowed to dry in air at 20° C. The degree of corrosion was then estimated visually. The criteria used to assign a particular corrosion level to a treated cord are set out hereafter in Notes to Table One.

TABLE One

| Example or Comp. Example | Material deposited on cord (a) | Solvents % volume | | | Corrosion level visual rating (b) |
|---|---|---|---|---|---|
| | | Ethanol | DMF | Toluene | |
| 20 | 1(B) | 90 | 10 | — | 4 |
| 21 | 2(B) | 80 | 20 | — | 3 |
| 22 | 3(B) | 75 | 25 | — | 3 |
| 23 | 4 | 75 | 25 | — | 2 |
| 24 | 5(B) | 84 | 16 | — | 6 |
| 25 | 6 | 84 | 16 | — | 8 |
| 26 | 7(B) | 84 | 16 | — | 3 |
| 27 | 8 | 90 | 10 | — | 4 |
| 28 | 9(B) | 84 | 16 | — | 1 |
| 29 | 10(B) | 76 | 24 | — | 0 |
| 30 | 11 | 90 | 10 | — | 1 |
| 31 | 12 | 100 | — | — | 7 |
| 32 | 13 | 50 | — | 50 | 0 |
| 33 | 14 | 84 | — | 16 | 2 |
| 34 | 15 | 84 | — | 16 | 5 |
| 35 | 16(B) | 100 | — | — | 7 |
| 36 | 17 | 100 | — | — | 3 |
| 37 | 18 | 100 | — | — | 2 |
| 38 | 19 | 70 | 30 | — | 6 |
| 39 | 1(B)50 2(B)45 | 85 | 15 | — | 3 |
| 40 | 1(B)45 2(B)45 17 10 | 86.5 | 13.5 | — | 5 |
| 41 | 1(B)40 2(B)40 17 20 | 88 | 12 | — | 1 |
| 42 | 1(B)33.3 2(B)33.3 17 33.3 | 90 | 10 | — | 2 |
| 43 | 3(B)50 4 50 | 75 | 25 | — | 1 |
| 44 | 3(B)40 4 40 17 20 | 80 | 20 | — | 1 |
| 45 | 9(B)50 17 50 | 92 | 8 | — | 1 |
| 46 | 9(B)40 10(B)40 17 20 | 84 | 16 | — | 0 |
| 47 | 16(B)50 2(B)50 | 90 | 10 | — | 6 |
| 48 | 16(B)40 2(B)40 17 20 | 92 | 8 | — | 6 |
| A | NONE | — | — | — | 9 |
| B | NONE | — | — | — | 10 |
| C | NONE | — | — | — | 10 |
| D | NONE | — | — | — | 9 |
| E | NONE | — | — | — | 8 |
| F | NONE | — | — | — | 10 |

Notes to Table One
(a) The number, or number and letter, refers to the example, or portion of the example, in which the preparation of the compound is described.

In Examples 39 to 48 a mixture of additives was used, and the number adjacent the reference to the additive refers to the percentage by weight of each additive in the mixture.

NONE indicates the wire had been degreased but not subjected to any further treatment.

(b) The corrosion level visual rating is as follows:

| Corrosion level visual rating | Description of cord after corrosion test |
|---|---|
| 9–10 | Very severe corrosion: very little evidence of a golden lustrous layer on the cord surface, which is covered with black and red corrosion products. |
| 7–8 | Severe corrosion: some isolated areas are still a lustrous golden colour. The corroded areas of the cord are mainly red with some black corrosion evident. |
| 5–6 | Some corrosion: approximately 50% of the cord has maintained the original lustrous sheen. In remaining areas red corrosion products predominate. |
| 3–4 | Slight corrosion: most of the cord is clean and lustrous. Occasional small areas of red corrosion are evident. |
| 1–2 | Trace corrosion: only the slightest evidence (a few red spots) are observed on the lustrous golden cord. |
| 0 | No corrosion: the shiny golden surface is unaffected, and is identical with untreated cord. |

EXAMPLES 49 to 65

Samples of single strand brass-coated steel wire, of the type used in reinforced car and truck tires, were cut into 40 cm lengths and degreased by immersion in 1,1,2,2-tetrachloroethylene at 120° C.

Products of some of Examples 1 to 19 were dissolved in 25 cm$^3$ of a suitable solvent (N,N-dimethylformamide or toluene) and the solutions diluted to a total volume of 200 cm$^3$ using industrial grade methylated spirits to give 0.2% w/v solutions of the additive.

The degreased wire samples (12 for each experiment) were immersed in the solutions prepared as described previously for 30 minutes at 50° C. The samples were then removed and rinsed with industrial grade methylated spirits. The treated wire samples were dried in air at ambient temperature and then stored in sealed glass tubes.

Ten wires were selected from each sample tube. The selected wires were moulded into an uncured SBR tire compound and the rubber was cured at 115° C. for 23 minutes, holding each wire in a straight position in the mould under a load of one kg.

The samples obtained were held for 24 hours at ambient temperature and split into two groups of five samples. One set of five was stored at 50±5% relative humidity and 23°±2° C. for 24 hours. The other set of five was placed in an autoclave having a steam saturated atmosphere at 120°±2° C. for 24 hours.

The two sets of samples were then subjected to tensile testing using the procedure described hereinafter.

Each sample was placed into a fixed slotted holder in such a manner that a wire was centrally orientated through the slot and was in the same axis as the pulling grip. The wire was then held by the pulling grip and pulled out of the moulded rubber block at a draw rate of 50 mm/minute.

The procedure was repeated for each wire moulded in the rubber. The tensile test was carried out at a temperature of 23°±2° C. The test procedure used corresponds generally with ASTM Test Method D 2229.

Further details of the material deposited on the wire and the results of the tensile tests are set out in Table Two.

TABLE Two

| Example or Comp. Example | Material deposited on cord (a) | Adhesion (N) Initial | Adhesion (N) Steam Aged |
| --- | --- | --- | --- |
| 49 | 1(B) | 220 | 57 |
| 50 | 2(B) | 231 | 70 |
| 51 | 3(B) | 220 | 47 |
| 52 | 4 | 210 | 54 |
| 53 | 5(B) | 238 | 58 |
| 54 | 6 | 247 | 67 |
| 55 | 7(B) | 205 | 62 |
| 56 | 8 | 224 | 72 |
| 57 | 9(B) | 248 | 41 |
| 58 | 10(B) | 247 | 88 |
| 59 | 11 | 163 | 78 |
| 60 | 12 | 205 | 24 |
| 61 | 14 | 175 | 33 |
| 62 | 16 | 238 | 70 |
| 63 | 17 | 216 | 62 |
| 64 | 18 | 210 | 53 |
| 65 | 19 | 143 | 39 |
| G | NONE | 219 | 58 |

I claim:

1. A compound which contains a ligand group selected from a triazole, a thiazole, a benzotriazole, a naphthotriazole, a 2-mercaptothiazole, or a 2-mercaptobenzothiazole and a group of the formula:

$$-NH-TAZ(NR_2)_2$$

or $$-NH-TAZ(NHR_2)_2$$

where
R is a hydrocarbyl group which is either a saturated hydrocarbyl group containing at least six but not more than 30 carbon atoms or an unsaturated hydrocarbyl group having a chain length of at least three but not more than 30 carbon atom; and
TAZ is a triazine ring.

2. A compound which contains a ligand group, selected from a benzothiazole, a 2-mercaptobenzothiazole, and a group of the formula:

$$-XR_n$$

where
X is a linking group, which contains at least one hereto-atom, selected from an amino, an amido, a carbonyloxy, a 1,4-phenylene, a substituted or unsubstituted triazinyl, and combinations of these groups;
R is a hydrocarbyl group which is either a saturated hydrocarbyl group containing at least six but not more than 30 carbon atoms or an unsaturated hydrocarbyl group having a chain length of at least three but not more than 30 carbon atom; and
n is an integer which has a value of at least one.

3. A compound selected from the group consisting of:
6(2,4-bis(allylamino)-s-triazin-6-ylamino)-2-mercaptobenzothiazole;
6(2,4-bis(diallylamino)-s-triazin-6-ylamino)-2-mercaptobenzothiazole;
5(2,4-bis(diallylamino)-s-triazin-6-ylamino)-benzotriazole;
5(2,4-bis(n-octadecylamino)-s-triazin-6-ylamino)-benzotriazole;
5(2,4-bis(di-n-octylamino)-s-triazin-6-ylamino)-benzotriazole; and
6(2,4-bis(di-n-octylamino)-s-triazin-6-ylamino)-2-mercaptobenzothiazole.

4. A compound in accordance with claim 3 wherein said compound is 6(2,4-bis(diallylamino)-s-triazin-6-ylamino)-2-mercaptobenzothiazole.

* * * * *